United States Patent
Park et al.

(10) Patent No.: US 9,155,793 B2
(45) Date of Patent: Oct. 13, 2015

(54) SKIN COMPOSITION FOR EXTERNAL USE CONTAINING CERAMIDES

(75) Inventors: Seung Han Park, Yongin-si (KR);
Byung Guen Chae, Yongin-si (KR);
Sang Hoon Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/342,967

(22) PCT Filed: Sep. 14, 2012

(86) PCT No.: PCT/KR2012/007378
§ 371 (c)(1),
(2), (4) Date: Mar. 5, 2014

(87) PCT Pub. No.: WO2013/039350
PCT Pub. Date: Mar. 21, 2013

(65) Prior Publication Data
US 2014/0220139 A1    Aug. 7, 2014

(30) Foreign Application Priority Data
Sep. 16, 2011 (KR) .................. 10-2011-0093634

(51) Int. Cl.
*A61K 9/16* (2006.01)
*A61K 47/26* (2006.01)
*A61Q 17/00* (2006.01)
*A61Q 19/00* (2006.01)
*A61K 9/00* (2006.01)
*A61K 9/127* (2006.01)
*A61K 31/16* (2006.01)
*A61K 47/18* (2006.01)
*A61K 31/164* (2006.01)

(52) U.S. Cl.
CPC ............... *A61K 47/26* (2013.01); *A61K 9/0014* (2013.01); *A61K 9/1274* (2013.01); *A61K 31/16* (2013.01); *A61K 31/164* (2013.01); *A61K 47/18* (2013.01); *A61Q 17/00* (2013.01); *A61Q 19/007* (2013.01)

(58) Field of Classification Search
CPC ............................. A61Q 17/00; A61Q 19/007
See application file for complete search history.

(56) References Cited

U.S. PATENT DOCUMENTS 7,169,382 B2    1/2007    Chopart et al.

FOREIGN PATENT DOCUMENTS

| KR | 10-2002-0076874 A | 10/2002 |
|---|---|---|
| KR | 10-0678790 B1 | 12/2006 |
| KR | 10-2010-0026143 A | 3/2010 |

OTHER PUBLICATIONS

Kim et al., "Formation and Dispersion of Stable Lamellar Structure Containing Ceramide," *J. Soc. Cosmet. Scientists Korea*, 35(3): p. 171-177 (Sep. 2009).
International Search Report for International Patent Application No. PCT/KR2012/007378 (mailed Feb. 13, 2013).

*Primary Examiner* — Carlos Azpuru
(74) *Attorney, Agent, or Firm* — Merchant & Gould P.C.

(57) ABSTRACT

The present invention provides a ceramide lamella structure comprising a glucoside surfactant, a preparation method thereof, and a skin composition for external use containing the same. According to the skin preparation composition for external use of the present invention, phase stability is very excellent and a greater amount of ceramides can be stably formed according to the stability of ceramides using multi-layered lamellar liquid crystals, thereby showing excellent skin moisturizing and skin barrier function repairing effects when applied to the skin.

12 Claims, 2 Drawing Sheets

SKIN COMPOSITION FOR EXTERNAL USE CONTAINING CERAMIDES

This application is a U.S. National Stage Application under 35 U.S.C. §371 of International Patent Application No. PCT/KR2012/007378, filed 14 Sep. 2012, which claims the benefit of priority to Korean Patent Application No. 10-2011-0093634, filed 16 Sep. 2011, the disclosures of all of which are hereby incorporated by reference in their entireties. The International Application was published in Korean on 21 Mar. 2013 as WO 2013/039350.

TECHNICAL FIELD

The present disclosure relates to a skin composition for external use containing ceramides, more particularly to a multilayered ceramide lamellar structure including a glucoside surfactant, wherein ceramides form multilayered lamellar liquid crystals, and exhibiting superior skin moisturizing effect, a method for preparing same and a composition for skin external use containing same.

BACKGROUND ART

The surface of human skin is composed of corneocytes, which are degenerated keratinocytes that have differentiated and grown from the basal layer. The corneocytes are bound by ceramide lamellar structures abundant in the stratum corneum and maintain the skin smooth and elastic.

Since ceramides are hardly soluble, they are prepared into small-sized particles when used in cosmetic products in large quantities. In this case, stability may decrease and gelation may occur. If the particle size is small, interparticle attraction increases greatly due to increased surface energy between particles. As a result, the ceramide particles tend to aggregate with each other, not being perfectly dispersed in an oil phase but being released into an aqueous phase. Gelation occurs as a result of the binding between the ceramide particles.

To solve this problem, granules prepared from ceramides, stearic acid, cholesterol, etc. are added at the last step of emulsion preparation to induce stabilization of ceramides. That is to say, by dispersing ceramides in an emulsion after stabilizing them by preparing into solid granules, the fluidity of the ceramides is removed and stability is improved. Korean Patent Application No. 2008-0072355 discloses ceramide granules including a shell solidified using a nucleation agent.

However, this method is problematic in that the amount of ceramides that can be used in a composition for skin external use is decreased because a large quantity of encapsulation agent has to be used for encapsulation of ceramides. In addition, use of the sugar- or polymer-based encapsulation agent impairs usability which is essential for the composition for skin external use.

DISCLOSURE

Technical Problem

In the present disclosure, gelation of ceramides due to particle aggregation is prevented by growing ceramides into larger particle size in advance, thereby stabilizing them and lowering surface energy, in order to solve the above-described problems. For this, the present disclosure is directed to providing a multilayered ceramide lamellar structure, which is prepared by stabilizing hardly soluble ceramides by forming multilayered lamellar liquid crystals under controlled cooling temperature, has very superior phase stability while having a structure similar to that of the stratum corneum of skin, capable of holding a large quantity of water and useful active substances and, thus, exhibits excellent skin moisturizing effect and skin barrier function recovering effect when applied to the skin, and a composition for skin external use containing same.

Technical Solution

In a general aspect, the present disclosure provides a ceramide lamellar structure including a glucoside surfactant.

In an exemplary embodiment of the present disclosure, the glucoside surfactant may be one or more selected from a group consisting of behenyl alcohol, arachidyl alcohol, arachidyl glucoside, a $C_{14-22}$ alcohol and a $C_{12-20}$ alkyl glucoside.

In an exemplary embodiment of the present disclosure, the ceramide lamellar structure may further include a wax or an oil.

In an exemplary embodiment of the present disclosure, the wax may be one or more selected from a group consisting of an alcohol, a fatty acid, a vegetable wax, a synthetic wax, ozokerite, cetyl palmitate, beeswax, a lipid and a lipopeptide.

In an exemplary embodiment of the present disclosure, the oil may be an ester oil or a hydrocarbon oil.

In an exemplary embodiment of the present disclosure, the ceramide may be one or more of a natural ceramide and a pseudoceramide.

In an exemplary embodiment of the present disclosure, the pseudoceramide may be one or more of the compounds represented by Chemical Formulas 1-5:

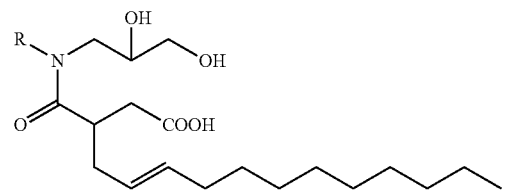

Chemical Formula 1 wherein R is a $C_9$-$C_{21}$ saturated or unsaturated aliphatic chain;

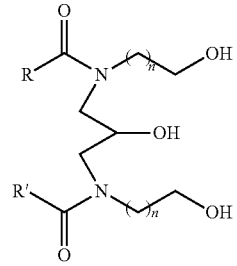

Chemical Formula 2 wherein n is 1 or 2; and each of R and R', which are identical or different, is independently a $C_9$-$C_{21}$ saturated or unsaturated aliphatic chain;

Chemical Formula 3

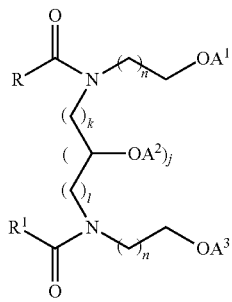

wherein each of m and n, which are identical or different, is independently an integer from 1 to 3;

each of k and l, which are identical or different, is independently 1 or 2;

j is 0 or 1;

each of R and R', which are identical or different, is independently a $C_1$-$C_{31}$ linear or branched, saturated or unsaturated alkyl group with or without a hydroxy group; and each of $A^1$, $A^2$ and $A^3$, which are identical or different, is independently hydrogen or one of the following substituents, with the proviso that $A^1$, $A^2$ and $A^3$ are not hydrogen at the same time:

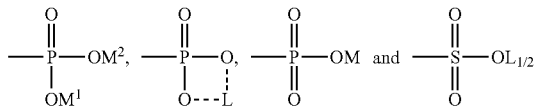

wherein each of M, $M^1$ and $M^2$, which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal;

Chemical Formula 4

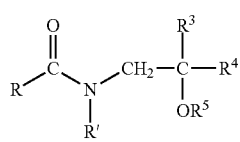

wherein each of R and R', which are identical or different, is independently a $C_{10}$-$C_{32}$ linear or branched, saturated or unsaturated alkyl group with or without a hydroxy group;

each of $R^3$ and $R^4$, which are identical or different, is independently hydrogen or a $C_1$-$C_4$ alkyl group or hydroxyalkyl group; and $R^5$ is -A or —$CH_2CH_2OA$, wherein A is one of the following substituents:

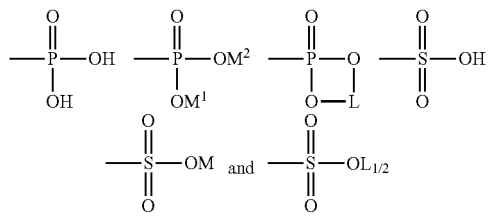

wherein each of M, $M^1$ and $M^2$, which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal; and Chemical Formula 5

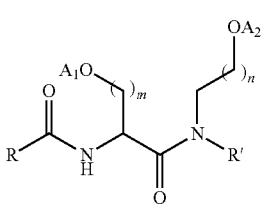

wherein each of m and n, which are identical or different, is independently an integer from 1 to 4;

each of R and R', which are identical or different, is independently a $C_1$-$C_{31}$ linear or branched, saturated or unsaturated alkyl group with or without a hydroxy group; and each of $A_1$ and $A_2$, which are identical or different, is independently hydrogen or one of the following substituents:

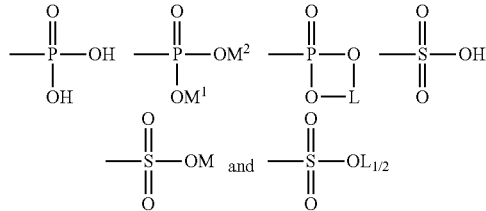

wherein each of M, $M^1$ and $M^2$, which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal.

In an exemplary embodiment of the present disclosure, the ceramide lamellar structure may be formed as the ceramide forms a plurality of lamellar layers.

In an exemplary embodiment of the present disclosure, the ceramide lamellar structure may have an average particle size of 2-30 µm.

In another general aspect, the present disclosure provides a composition for skin external use, containing the ceramide lamellar structure.

In an exemplary embodiment of the present disclosure, the ceramide may be contained in an amount of 0.01-20 wt % based on the total weight of the composition.

In an exemplary embodiment of the present disclosure, the composition may be for moisturizing skin or enhancing skin elasticity.

In an exemplary embodiment of the present disclosure, the composition may be a cosmetic composition or a pharmaceutical composition.

In another general aspect, the present disclosure provides a method for preparing a ceramide lamellar structure, including: mixing an oil-phase solution containing a ceramide, an aqueous-phase solution and a glucoside surfactant; and keeping the resulting mixture solution at 45-60° C.

In an exemplary embodiment of the present disclosure, the ceramide lamellar structure may be formed by the glucoside surfactant.

Advantageous Effects

A composition for skin external use of the present disclosure has very superior phase stability because ceramides are stabilized by forming multilayered lamellar liquid crystals. Since a greater amount of ceramides can be formed stably, the composition provides excellent skin moisturizing effect and skin barrier function recovering effect when applied to the skin.

BEST MODE FOR CARRYING OUT INVENTION

Figure 1:
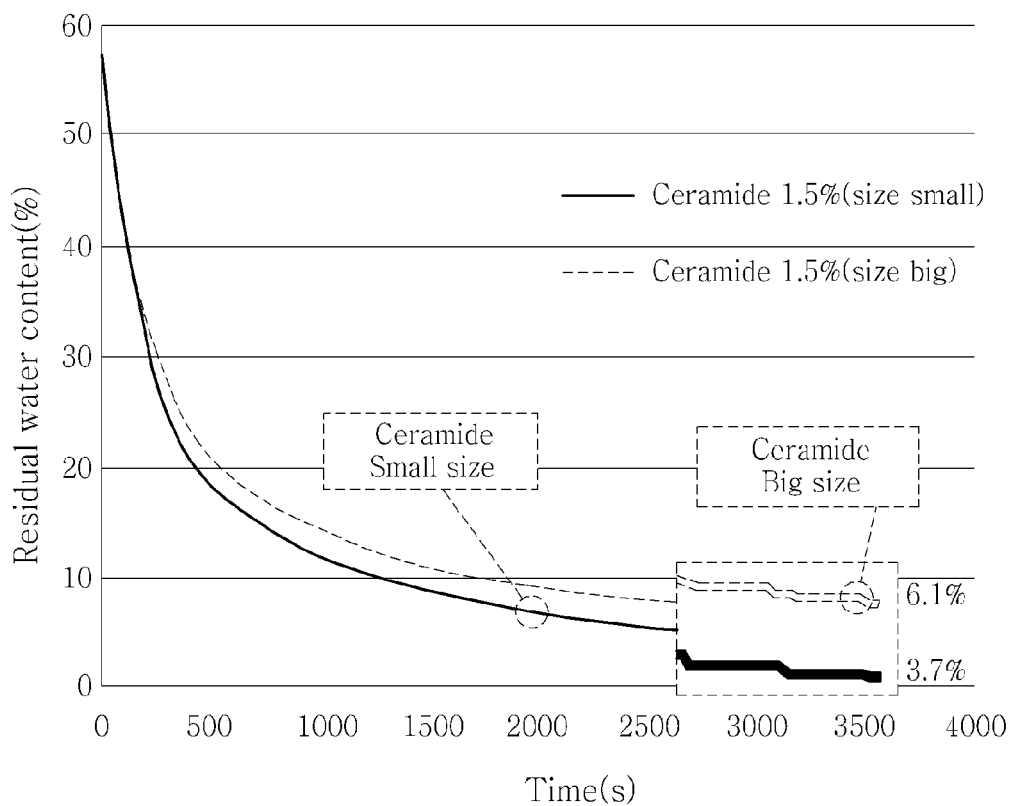
FIG. 1 shows the effect of preventing evaporation of water from artificial leather by a composition for skin external use according to an exemplary embodiment of the present disclosure depending on the particle size of the ceramide liquid crystal.

Hereinafter, specific embodiments of the present disclosure are described in detail so that those of ordinary skill in the art to which the present disclosure belongs can easily carry out the present disclosure.

The present disclosure provides a multilayered ceramide lamellar structure including a glucoside surfactant.

The lamellar structure consists of multilayered liquid crystals and includes a ceramide and a glucoside surfactant.

The structure has a hydrophilic outside and a hydrophobic inside, and the surfactant is located between the hydrophilic outside and the hydrophobic inside.

In the present disclosure, the glucoside surfactant is used as a surfactant. Specifically, a lecithin-based, glucoside-based or sorbitan-based surfactant may be used to form the liquid crystals. However, it is difficult to achieve the particle size described in the present disclosure with the lecithin- and sorbitan-based surfactants because they lead to small particle size. The glucoside surfactant is advantageous in that large-sized liquid crystals can be formed and long-term stability can be ensured.

The glucoside surfactant used in the present disclosure may be one or more selected from a group consisting of behenyl alcohol, arachidyl alcohol, arachidyl glucoside, a $C_{14-22}$ alcohol and a $C_{12-20}$ alkyl glucoside, although not being limited thereto.

In addition, the multilayered ceramide lamellar structure may further include a wax or an oil. The wax and oil help the formation of firm interfacial layers and are provided in the surfactant.

The wax is not particularly limited as long as it is one commonly used in creams. Specifically, it may be one or more selected from a group consisting of an alcohol, a fatty acid, a vegetable wax, a synthetic wax, ozokerite, cetyl palmitate, beeswax, a lipid and a lipopeptide.

Although the oil is not particularly limited, it may be specifically an ester oil or a hydrocarbon oil. Specifically, the ester oil may be isopropyl myristate, isopropyl palmitate, octyl dodecyl myristate, cetyl octanoate, cetyl 2-ethylhexanoate, a $C_{14-18}$ alkyl ethylhexanoate, coco-caprylate/caprate or decyl cocoate, or a diester oil such as butylene glycol dicaprylate/dicaprate, diisostearyl malate, a di-$C_{12-13}$ alkyl malate, neopentyl glycol diheptanoate, tridecyl stearate, neopentyl glycol dicaprylate/dicaprate, tridecyl trimellitate and dicaprylyl carbonate. The hydrocarbon oil may be hydrogenated polyisobutene, hydrogenated polydecene or squalane.

In the present disclosure, the ceramide may be one or more selected from a group consisting of a natural ceramide and a pseudoceramide.

The natural ceramide is a naturally occurring ceramide and includes ceramide 1, ceramide 2, ceramide 3, ceramide 4, ceramide 5, ceramide 6, ceramide 7, ceramide 8, etc. The pseudoceramide includes ceramide 104, ceramide 102, etc.

In the present disclosure, the pseudoceramide collectively refers to compounds having the double-chain lamellar structure of the natural ceramide.

In the present disclosure, the lamellar structure prevents gelation of the pseudoceramide from outside. If the lamellar structure forms multi-lamellar layers of two or more layers, thereby forming a macroemulsion, the ceramide can be stabilized and superior spreadability and light usability may be achieved.

Rod-type SAAs including ceramides are mostly known to be more stable as the curvature is smaller, or the radius of curvature is larger. Accordingly, macroemulsions of small curvature are more stable than emulsions of larger curvature and smaller particle size.

Figure 2:
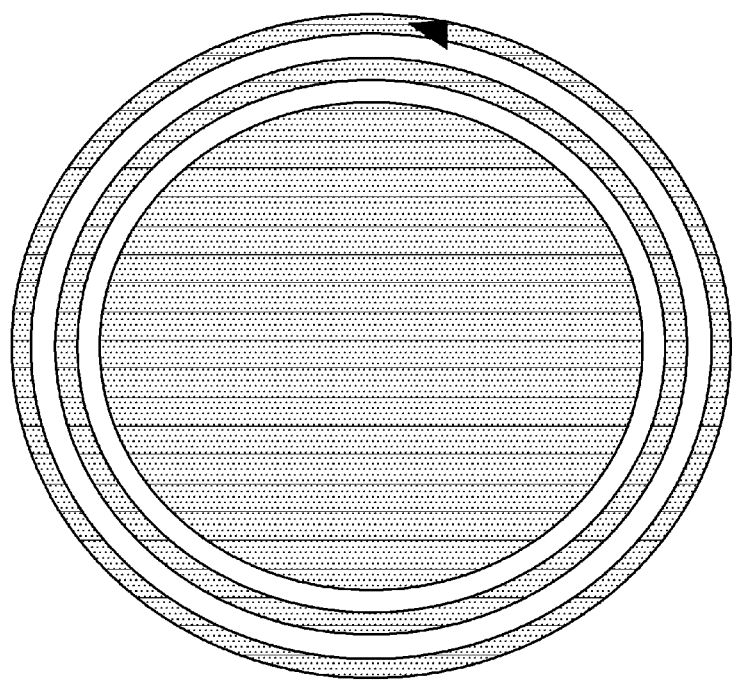
FIG. 2 shows a multilayered lamellar structure included in a composition for skin external use according to an exemplary embodiment of the present disclosure.

FIG. 2 shows a multilayered lamellar structure included in a composition for skin external use according to an exemplary embodiment of the present disclosure. It is known that the stability is increased by 5 times as the number of the lamellar layer increases by one.

Specifically, the pseudoceramide may be one or more of the compounds represented by Chemical Formulas 1-5, although not being limited thereto:

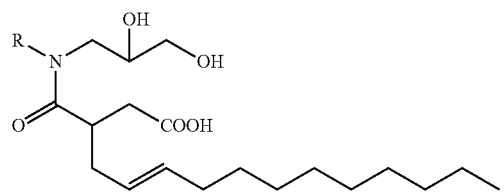

Chemical Formula 1 wherein R is a $C_9$-$C_{21}$ saturated or unsaturated aliphatic chain;

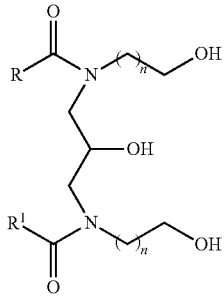

Chemical Formula 2 wherein n is 1 or 2; and each of R and R', which are identical or different, is independently a $C_9$-$C_{21}$ saturated or unsaturated aliphatic chain;

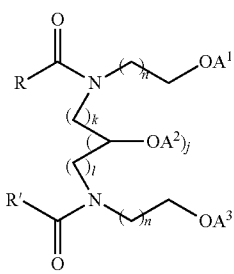

Chemical Formula 3 wherein each of m and n, which are identical or different, is independently an integer from 1 to 3;

each of k and l, which are identical or different, is independently 1 or 2;

j is 0 or 1;

each of R and R', which are identical or different, is independently a $C_1$-$C_{31}$ linear or branched, saturated or unsaturated alkyl group with or without a hydroxy group; and each of $A^1$, $A^2$ and $A^3$, which are identical or different, is independently hydrogen or one of the following substituents, with the proviso that $A^1$, $A^2$ and $A^3$ are not hydrogen at the same time:

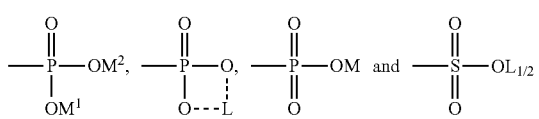

wherein each of M, $M^1$ and $M^2$, which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal;

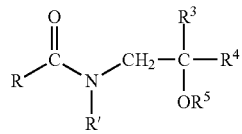

Chemical Formula 4 wherein each of R and R', which are identical or different, is independently a $C_{10}$-$C_{32}$ linear or branched, saturated or unsaturated alkyl group with or without a hydroxy group;

each of $R^3$ and $R^4$, which are identical or different, is independently hydrogen or a $C_1$-$C_4$ alkyl group or hydroxyalkyl group; and $R^5$ is -A or —$CH_2CH_2OA$, wherein A is one of the following substituents:

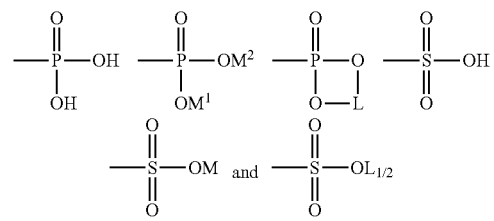

wherein each of M, $M^1$ and $M^2$, which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal; and

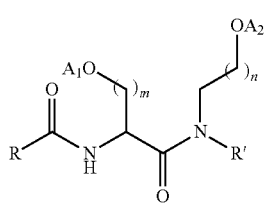

Chemical Formula 5 wherein each of m and n, which are identical or different, is independently an integer from 1 to 4;

each of R and R', which are identical or different, is independently a $C_1$-$C_{31}$ linear or branched, saturated or unsaturated alkyl group with or without a hydroxy group; and each of $A_1$ and $A_2$, which are identical or different, is independently hydrogen or one of the following substituents:

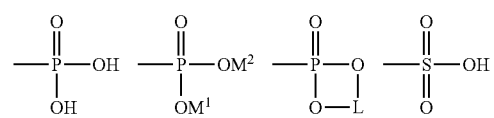

-continued

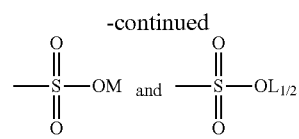

wherein each of M, M¹ and M², which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal.

The compounds represented by Chemical Formulas 1-5 are pseudoceramides having superior skin moisturizing and skin barrier function recovering effects.

In the present disclosure, the multilayered ceramide lamellar structure, i.e. the multilayered lamellar liquid crystals, refer to a macroemulsion. Specifically, the multilayered ceramide lamellar structure, i.e. the multilayered lamellar liquid crystals, may have an average particle size of 2-30 μm. The pseudoceramide may be stabilized and satisfactory usability and improved moisturizing effect may be achieved when the average particle size of the multilayered ceramide lamellar structure is 2 μm or greater. If the average particle size exceeds 30 μm, stability may be unsatisfactory.

The present disclosure also provides a composition for skin external use containing the multilayered ceramide lamellar structure.

The composition for skin external use may contain a ceramide in an amount of 0.01-20 wt %, more specifically 0.05-10 wt %, based on the total weight of the composition. The above-described range is very effective in skin moisturization and barrier function recovery since very superior phase stability and water holding ability can be achieved. If the ceramide content is less than 0.01%, it is difficult to achieve desired hydrating and moisturizing ability. And, if it exceeds 20%, it is difficult to maintain stability.

The composition of the present disclosure may contain a hardly soluble substance, which may be ceramide 3B, in the composition up to a certain amount owing to the lamellar structure.

The composition for skin external use according to the present disclosure may be a composition for skin external use for moisturizing skin or enhancing skin elasticity. Since the multilayered lamellar liquid crystals formed by ceramides result in increased water content and improved skin barrier recovering effect as described above, the composition may be usefully used for moisturizing skin and enhancing skin elasticity.

The composition for skin external use according to the present disclosure may be prepared by a method for preparing a multilayered ceramide lamellar structure, including: mixing an oil-phase solution containing a ceramide, an aqueous-phase solution and a glucoside surfactant; and keeping the resulting mixture solution at 45-60° C.

The multilayered ceramide lamellar structure may be formed by the glucoside surfactant. In the present disclosure, the glucoside surfactant may be one or more selected from a group consisting of behenyl alcohol, arachidyl alcohol, arachidyl glucoside, a $C_{14-22}$ alcohol and a $C_{12-20}$ alkyl glucoside, although not being limited thereto.

By maintaining cooling temperature at 45-60° C. when multilayered lamellar liquid crystals are formed, particle size providing the best skin moisturizing effect may be achieved.

If the cooling temperature is below 45° C., the lamellar structure may not be formed because a wax and an oil may exist in an inner phase, not at an interface. And, if the cooling temperature is above 60° C., cooling may not proceed as desired because the temperature is above the melting point of the wax and the oil. That is to say, the wax and the oil may be sufficiently present at the interface when the cooling temperature is 45-60° C. and multilayered lamellar liquid crystals having an average particle size of 2-30 μm may be formed when cooling is performed within the temperature rage. Multilayered lamellar liquid crystals having an average particle size of 2-30 μm may contribute to stabilization of a pseudoceramide. In addition, outside the above temperature range, particle size may become nonuniform and the stability of the final composition may be unsatisfactory.

More uniform particle size and hence better stability of the composition may be achieved when cooling is performed in the temperature range specifically for 5-60 minutes, more specifically for 10-40 minutes.

The composition for skin external use according to the present disclosure may be, for example, a pharmaceutical composition or a cosmetic composition.

The pharmaceutical composition may further include a pharmaceutical adjuvant or other therapeutically useful substance such as a preservative, a stabilizer, a wetting agent, an emulsifier, a salt and/or a buffer for osmotic control, etc. and may be formulated into various parenteral administration forms according to methods known in the art. A formulation for parenteral administration may be one for transdermal administration, for example, lotion, ointment, gel, cream, patch or spray, although not being limited thereto.

Determination of the administration dosage of the active ingredient is within the level of those skilled in the art. A daily administration dosage will vary depending on various factors including the particular condition, age, physical condition of the subject, absence or presence of complication(s), etc. For an adult, a general daily administration dosage of the composition is from 1 μg/kg to 200 mg/kg, specifically from 50 μg/kg to 50 mg/kg, once to three times a day. However, this administration dosage does not limit the scope of the present disclosure by any means.

Formulations of the cosmetic composition are not particularly limited but may be selected properly depending on purposes. For example, the composition may be prepared into one or more formulation selected from a group consisting of softening lotion (skin lotion and milk lotion), nourishing lotion, essence, nourishing cream, massage cream, pack, gel, eye cream, eye essence, cleansing cream, cleansing foam, cleansing water, powder, body lotion, body cream, body oil and body essence, although not being limited thereto.

The content of the active ingredient is not particularly limited but may be 0.01-10 wt % based on the total weight of the composition. A superior effect may be achieved without side effects when the content of the active ingredient satisfies the above condition.

The cosmetic composition may further contain a cosmetically acceptable excipient serving as a diluent, a dispersant or a carrier such that the composition can be uniformly applied on skin. Specifically, the composition may be an oil-in-water (O/W) emulsion, and the emulsion may contain at least 80 wt % of water as an excipient. However, without being limited thereto, any known cosmetically acceptable excipient may also be used.

The cosmetic composition may contain various cosmetic adjuvants commonly used in the related art such as a fatty substance, an organic solvent, silicon, a thickener, an emollient, a sunscreen agent, an antifoaming agent, a moisturizing agent, a perfume, a preservative, a surfactant, a filler, a sequestrant, a cationic, anionic, nonionic or amphoteric polymer or a mixture thereof, a propellant, an alkalizing or acidifying agent, a dye, a pigment or nanopigment (especially, one prepared to supplementally provide sunscreen effect by physically blocking UV radiation) or other components commonly used in cosmetics, especially in sunscreen compositions.

The organic solvent may be, for example, a lower alcohol or a polyol, e.g., ethanol, isopropanol, propylene glycol, glycerol, sorbitol, etc.

The fatty substance may be, for example, an oil, a wax or a mixture thereof, a fatty acid, a fatty acid ester, a fatty alcohol, petrolatum, a paraffin, lanolin, hydrogenated lanolin or acetylated lanolin. The oil may be an animal, vegetable, mineral or synthetic oil and may be selected, especially, from hydrogenated palm oil, hydrogenated castor oil, liquid petrolatum, liquid paraffin, purcellin oil, volatile or nonvolatile silicon oil and isoparaffin.

When the cosmetic composition is a sunscreen composition for protecting the skin from UV, it may be in the form of a suspension or a dispersion of a solvent or a fatty substance. Alternatively, it may be in the form of a cream, an emulsion (in particular, oil-in-water (O/W) or water-in-oil (W/O), specifically O/W, emulsion), a vesicular dispersion, an ointment, a gel, a solid stick or an aerosol foam. The emulsion may further contain an anionic, nonionic, cationic or amphoteric surfactant.

When the cosmetic composition is used to protect hair, it may be in the form of a shampoo, a lotion, a gel or a rinse and may be used before or after hair washing, before or after dyeing or bleaching, or before, during or after wave perming or straight perming. It may also be in the form of a lotion or gel for styling or treatment, a lotion or gel for hair drying or setting, a hair lacquer, a composition for hair waving or straight perming, or a composition for hair dyeing or bleaching.

When the cosmetic composition is used as a makeup product for eyelashes, eyebrows, skin or hair, e.g., a cream for treating skin, a foundation cream, a lipstick, an eye shadow, a blusher, an eyeliner, a mascara, a coloring gel, etc., it may be in the form of an anhydrous or aqueous solid or paste, e.g., oil-in-water or water-in-oil emulsion, suspension or gel.

The present disclosure also provides an agent for treating a skin disease, containing the composition for skin external use. The skin disease is not particularly limited but may be, for example, acne, psoriasis, hair loss, dead skin disorder, etc.

The present disclosure also provides an agent for skin external use containing the composition for skin external use. The agent for skin external use includes any one that can be externally applied to the skin. Various types of cosmetics and medicines may be included therein. The agent for skin external use may be, for example, an agent for skin external use for preventing skin aging or improving skin wrinkles, although not being particularly limited thereto.

Hereinafter, the present disclosure will be described in detail through examples. However, the following examples are for illustrative purposes only and the scope of the present disclosure is not limited by the examples.

Example 1 and Comparative Example 1

TABLE 1

| Ingredients | wt % |
|---|---|
| 1. Butylene glycol dicaprylate/dicaprate | 4.00 |
| 2. Hydroxypropyl bislauramide MEA (Pc104) | 0.70 |
| 3. Hydroxypropyl bispalmitamide MEA (Pc102) | 0.80 |
| 4. Cholesterol | 0.50 |
| 5. Stearic acid | 1.50 |
| 6. Behenyl alcohol | 2.00 |
| 7. Behenyl alcohol, arachidyl alcohol, arachidyl glucoside | 1.00 |
| 8. $C_{14-22}$ alcohol, $C_{12-20}$ alkyl glucoside | 1.00 |
| 9. Pentaerythritol triisostearate | 4.00 |
| 10. Cetyl ethylhexanoate | 3.00 |
| 11. Squalane | 3.00 |
| 12. Cyclopentasiloxane | 4.00 |
| 13. Cyclopentasiloxane, dimethiconol | 1.00 |
| 14. Purified water | To 100 |
| 15. Glycerin | 5.00 |
| 16. Butylene glycol | 10.00 |
| 17. Tromethamine | 0.05 |
| 18. Preservative | adequate |

<Preparation Method>

1) The ingredients 1-13 were mixed according to the composition described in Table 1 and were dissolved at 75° C. to prepare an oil-phase solution. Hydroxypropyl bislauramide MEA (Pc104) and hydroxypropyl bispalmitamide MEA (Pc102) were included as pseudoceramides.

2) In a separate container, the ingredients 14-18 described in Table 1 were mixed and dissolved at 75° C. to prepare an aqueous-phase solution.

3) The oil-phase solution of 1) was added to the aqueous-phase solution of 2) and the mixture was stirred using a homogenizing mixer.

4) In Example 1, a cooling temperature of about 52° C. was maintained for about 35 minutes. In Comparative Example 1, the mixture was cooled rapidly to 30° C. within 5 minutes.

5) Cosmetic compositions of Example 1 and Comparative Example 1 were prepared by removing foams from the mixtures of 4).

Test Example 1

Stability of Compositions

The difference in the stability of the compositions of Example 1 and Comparative Example 1 owing to difference in particle size caused by the difference in cooling temperature was tested as follows. In order to investigate the stability of the compositions of Example 1 and Comparative Example 1, the compositions were observed while keeping under cold condition (4° C.), freezing condition (−18° C.) and in water baths of 30° C. and 45° C. The result is given in Table 2.

TABLE 2

|  | Cold (4° C.) | Freezing (−18° C.) | 30° C. | 45° C. |
|---|---|---|---|---|
| Example 1 | Stable | Stable | Stable | Stable for 6 months |
| Comparative Example 1 | Stable | Stable | Unstable | Gelation occurred |

As seen from Table 2, the composition of Comparative Example 1 showed gelation at 45° C. because of too small particle size caused by rapid cooling.

In contrast, the composition of Example 1 showed very superior phase stability, being stable for 6 months at 45° C., because multilayered lamellar liquid crystals having a particle size of 2 μm or greater were formed. This demonstrates that the multilayered lamellar liquid crystals formed under controlled cooling temperature exhibit very superior effect of preventing gelation of the composition containing pseudoceramides.

Test Example 2

Evaporation of Water

The difference in evaporation of water depending on the particle size of pseudoceramide-containing liquid crystals and the absence or presence of pseudoceramides was tested using the compositions of Example 1 and Comparative Example 1.

<Test Method>

Evaporation of water with time was measured using a humidity controller and an electronic balance. More specifically, the experimental environment was controlled to R.H. 29±1% using a desiccator and experiment was conducted in a constant-temperature, constant-humidity laboratory at 24±2° C. Under this constant temperature and humidity condition, the change in weight of artificial leather (25 cm$^2$, 35 mg) on which 290 mg of the composition of Example 1 or Comparative Example 1 was applied was monitored for 1 hour. The result is shown in FIG. 1.

As seen from FIG. 1, the composition of Example 1 having the largest particle size showed the highest residual water content.

The slope of the curved region is an indicator of the evaporation rate of bound water. The smaller this value, the longer water is held. The composition of Example 1 also showed the best result in the slope, followed by the composition of Comparative Example 1 containing pseudoceramides but having a smaller liquid crystal size. The test demonstrated that the pseudoceramide-containing multilayered lamellar liquid crystals slow the rate of water evaporation, thereby increasing residual water content.

We claim:

1. A ceramide lamellar structure comprising a glucoside surfactant, wherein the ceramide lamellar structure has an average particle size of 2-30 μm.

2. The ceramide lamellar structure according to claim 1, wherein the glucoside surfactant is one or more selected from a group consisting of behenyl alcohol, arachidyl alcohol, arachidyl glucoside, a $C_{14-22}$ alcohol and a $C_{12-20}$ alkyl glucoside.

3. The ceramide lamellar structure according to claim 1, wherein the ceramide lamellar structure further comprises a wax or an oil.

4. The ceramide lamellar structure according to claim 3, wherein the wax is one or more selected from a group consisting of an alcohol, a fatty acid, a vegetable wax, a synthetic wax, ozokerite, cetyl palmitate, beeswax, a lipid and a lipopeptide.

5. The ceramide lamellar structure according to claim 3, wherein the oil is an ester oil or a hydrocarbon oil.

6. The ceramide lamellar structure according to claim 1, wherein the ceramide is one or more of a natural ceramide and a pseudoceramide.

7. The ceramide lamellar structure according to claim 6, wherein the pseudoceramide is one or more of the compounds represented by Chemical Formulas 1-5:

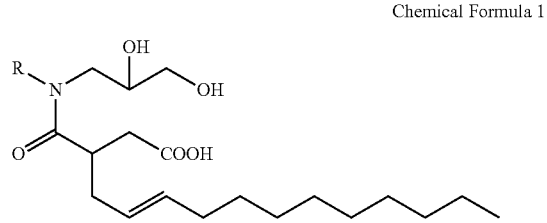

Chemical Formula 1 wherein R is a $C_9$-$C_{21}$ saturated or unsaturated aliphatic chain;

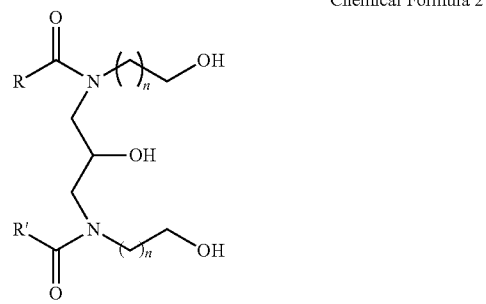

Chemical Formula 2 wherein n is 1 or 2; and each of R and R', which are identical or different, is independently a $C_9$-$C_{21}$ saturated or unsaturated aliphatic chain;

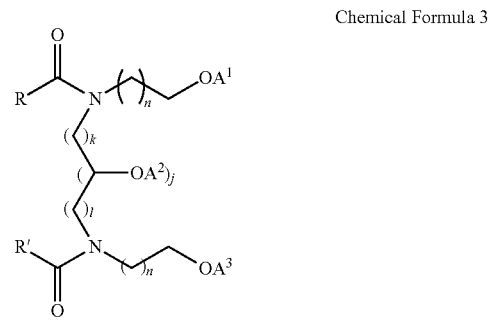

Chemical Formula 3 wherein each of m and n, which are identical or different, is independently an integer from 1 to 3;

each of k and l, which are identical or different, is independently 1 or 2;

j is 0 or 1;

each of R and R', which are identical or different, is independently a $C_1$-$C_{31}$ linear or branched, saturated or unsaturated alkyl group with or without a hydroxy group; and each of $A^1$, $A^2$ and $A^3$, which are identical or different, is independently hydrogen or one of the following substituents, with the proviso that $A^1$, $A^2$ and $A^3$ are not hydrogen at the same time:

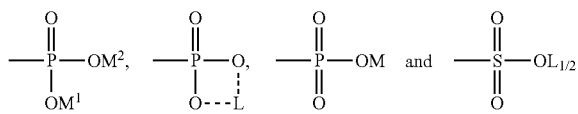

wherein each of M, M¹ and M², which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal;

Chemical Formula 4

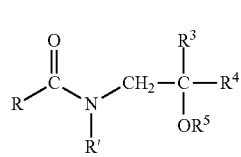

wherein each of R and R', which are identical or different, is independently a $C_{10}$-$C_{32}$ linear or branched, saturated or unsaturated alkyl group with or without a hydroxy group;

each of $R^3$ and $R^4$, which are identical or different, is independently hydrogen or a $C_1$-$C_4$ alkyl group or hydroxyalkyl group; and $R^5$ is -A or —CH₂CH₂OA, wherein A is one of the following substituents:

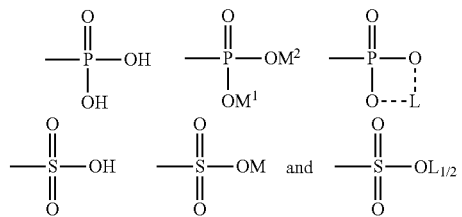

wherein each of M, M¹ and M², which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal; and Chemical Formula 5

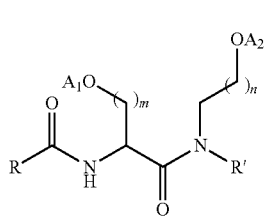

wherein each of m and n, which are identical or different, is independently an integer from 1 to 4;

each of R and R', which are identical or different, is independently a $C_1$-$C_{31}$ linear or branched, saturated or unsaturated alkyl group with or without a hydroxy group; and each of $A_1$ and $A_2$, which are identical or different, is independently hydrogen or one of the following substituents:

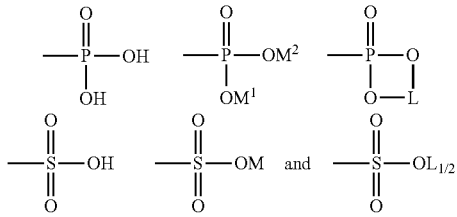

wherein each of M, M¹ and M², which are identical or different, is independently selected from a group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal.

8. The ceramide lamellar structure according to claim 1, wherein the ceramide lamellar structure is formed as the ceramide forms a plurality of lamellar layers.

9. A composition for skin external use, comprising the ceramide lamellar structure according to claim 1.

10. The composition for skin external use according to claim 9, wherein the ceramide is contained in an amount of 0.01-20 wt % based on the total weight of the composition.

11. A method comprising transdermally administering the composition according to claim 9 to a subject in need thereof, wherein the method is for moisturizing skin or enhancing skin elasticity.

12. The composition for skin external use according to claim 9, wherein the composition is a cosmetic composition or a pharmaceutical composition.

* * * * *